United States Patent [19]

Kipnis

[11] Patent Number: 4,738,268

[45] Date of Patent: Apr. 19, 1988

[54] RELATIVE TIME CLOCK

[75] Inventor: Gary D. Kipnis, Corona Del Mar, Calif.

[73] Assignee: Tokos Medical Corporation, Irvine, Calif.

[21] Appl. No.: 40,293

[22] Filed: Apr. 20, 1987

Related U.S. Application Data

[63] Continuation of Ser. No. 758,382, Jul. 24, 1985, abandoned.

[51] Int. Cl.⁴ .......... A61B 5/04

[52] U.S. Cl. .......... 128/775; 128/778; 128/904

[58] Field of Search .......... 128/904, 782, 775, 778, 128/690; 364/143, 145, 146

[56] References Cited

U.S. PATENT DOCUMENTS

| | | | |
|---|---|---|---|
| Re. 29,642 | 5/1978 | Kwiatkowski et al. | 364/143 |
| 3,742,938 | 7/1973 | Stern | 128/904 |
| 3,877,466 | 4/1975 | Montor | 128/732 |
| 3,972,320 | 8/1976 | Kalman | 128/690 |
| 4,114,188 | 9/1978 | Carter et al. | 128/778 |
| 4,173,971 | 11/1979 | Karz | 128/904 |
| 4,216,462 | 8/1980 | McGrath et al. | 128/904 |
| 4,346,718 | 8/1982 | Morris | 128/710 |
| 4,422,081 | 12/1983 | Woods | 128/710 |
| 4,428,381 | 1/1984 | Hepp | 128/904 |
| 4,458,693 | 7/1984 | Badzinski et al. | 128/904 |

*Primary Examiner*—Edward M. Coven
*Attorney, Agent, or Firm*—Lyon & Lyon

[57] ABSTRACT

There is disclosed herein a relative time clock wherein the relative time between two or more events is recorded independently of real time or wall clock time. A continuous time clock will count in units such as days, hours, minutes and seconds until the clock reaches a predetermined maximum time at which point the continuous time clock will reset and repeat its previous count cycle. The time indicated on the continuous time clock is recorded and correlated to events such as the start and finish of a data recording. A final event, such as a data transfer, is also correlated to the time indicated on the continuous time clock. After this date is processed, the relative time of any event can be determined with respect to any other event.

5 Claims, 2 Drawing Sheets

LEGEND:
ET = EVENT TIME
00:00:00 = DAYS: HOURS: MINUTES

RELATIVE TIME CLOCK

This is a continuation of co-pending application Ser. No. 758,382, filed on July 24, 1985, now abandoned.

BACKGROUND

The relative time clock is a mechanism designed for applications where the relative time between two or more events is important. It is especially useful in medical applications, where the age of datum is often more useful than the actual time that its capture took place. For instance, a doctor may wish to monitor the preterm uterine activity of a patient on a daily or twice daily basis for a period of a week. It would be inconvenient for a patient to make two daily trips to the doctor's office. Also the doctor may wish to have readings taken at times when the doctor's office is not normally open. It would be more efficient as well as convenient for the patient to make daily recordings at home, at various times, and then transmit that data at a later time over the phone lines to the doctor's office. In such an instance the doctor may want to know how long ago the various sets of data were recorded. By monitoring the relative time between the occurrence of various events the doctor will be able to determine age of the datum he is analyzing. The abovementioned events are detected by means of a pressure transducer such as the one disclosed in the patent application for a Pressure Transducer filed in the name of Charles S. Mitchell and filed with the U.S. Patent and Trademarks Office on Feb. 15, 1985, the disclosure of which is incorporated herein by reference.

SUMMARY OF THE INVENTION

In accordance with the present invention, a device and method is disclosed for recording the relative time between two or more events.

The mechanism is based on a continuous time clock which counts in units of days, hours, minutes, seconds and tenths of seconds on a continuous basis. When an event occurs, such as start of a data recording, the time registered by the continuous time clock is correlated with that event. When subsequent events occur, such as particular data readings or the end of a data reading, the time registered by the continuous time clock is also correlated with those events. The final event in any sequence of events would normally be the transmission of the recorded data to a doctor's office for analysis. The relative time between that last event and any previous event can be calculated by subtracting the previous event time from the last event time. It is then possible for the doctor to determine how long ago any particular event occurred, independent of wall clock time. Similarly, if the doctor or technician records the actual wall clock time when the data is transferred, then the wall clock time when any particular event occurred can be reconstructed.

Accordingly, a principal object of this invention is to provide a portable system for recording data and determining the age of that data with respect to other events in a manner independent of wall clock time.

Another object of this invention is to provide a system wherein no user interaction is required to initialize the continuous time clock and wherein the wall clock time of a past event can be reconstructed if desired.

BRIEF DESCRIPTION OF THE DRAWINGS

These and other objects and features of the present invention will become better understood through a consideration of the following description taken in conjunction with the drawings in which.

DETAILED DESCRIPTION

Figure 1:
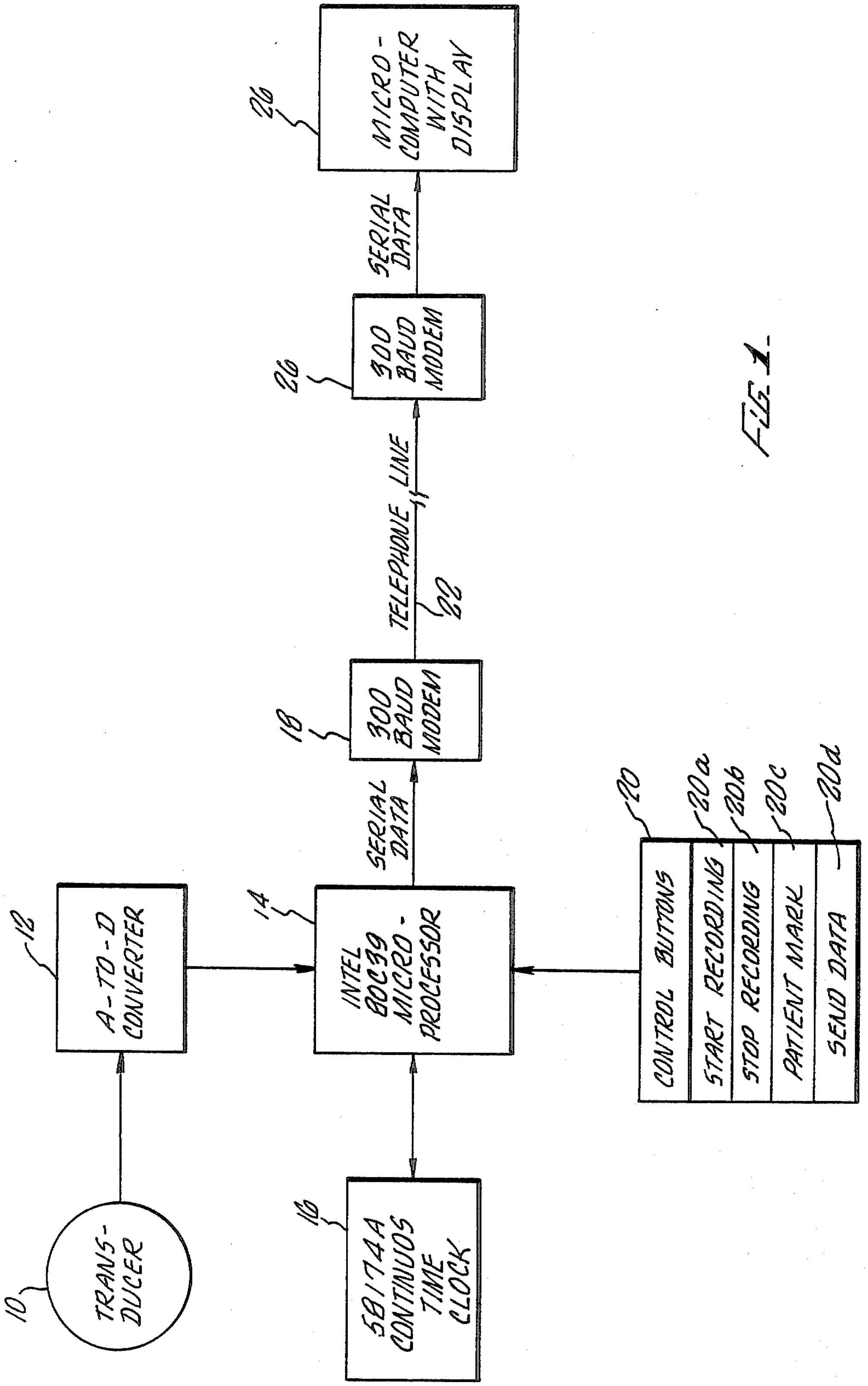
FIG. 1 shows a block diagram of an electronic system and related electronic hardware that incorporates the use of a relative time clock.

Turning now to the drawings, FIG. 1 is a block diagram showing the various elements of a system incorporating a relative time clock. A transducer 10 is a pressure sensitive transducer which is designed to convert pressure changes characteristic of uterine activity during the preterm period of a pregnancy. Transducer 10 is of the type disclosed in the previously referenced patent application for a Pressure Transducer. The transducer 10 senses uterine pressure and develops an analog voltage signal which corresponds to changes in preterm uterine pressure. The analog signal from the transducer 10 is fed into an analog to digital (A to D) converter 12 with an eight bit parallel output. The binary output of the A to D converter 12 representing numbers 0 to 251 are reserved for pressure data output and numbers 252 to 255 are invalid as pressure data numbers and are reserved for the recording of special events such as "start data recording" and "patient mark". The output from the analog to digital converter 12 is fed into a microprocessor 14 which is typically an Intel 80C39 microprocessor. The continuous time clock 16, typically a National Semiconductor MM58174A, is capable of keeping track of days, hours, minutes, seconds and tenths of seconds on a continuous basis. The 58174A contains all the registers necessary to build the continuous time clock 16 with a small amount of software control. The continuous time clock 16 will count in units of days, hours, minutes, seconds and tenths up to a point where the continuous time clock 16 is reset and the process is started anew. The number of days, or weeks, that the continuous time clock will count is determined by the largest relative time that needs to be kept. For example, if data is saved by an instrument for a maximum of three days, then the days register will count from zero through at least three in order to calculate relative time up to three days. When the days register reaches the maximum number of days in its cycle, the next tick of the clock wraps it around back to day zero. The hours, minutes, seconds and tenths registers work in a similar manner, with hours running from zero to 23, minutes and seconds running from 0 to 59 and tenths running from 0 to 9. The carry out of each stage, except the days register, is used as a count enable for the next stage.

The control buttons 20*a* to 20*c* perform three basic functions. There is a button 20*a* for starting the data recording, a button 20*b* for stopping the data recording and a button 20*c* that allows a patient to indicate that she believes a certain event is taking place. When button 20*c* is depressed, a time stamp is added to the data that is recorded at that particular moment so that a later analysis will reveal whether or not the patient's observations correspond with the data that has been collected. The microprocessor 14, in the present embodiment, stores data in the form of 8-bit words. The bits representing numbers 0 to 251 represent the digital information corresponding to pressure variations detected by the transducer 10 and converted by the A to D converter 12. For example, bits representing the number 0 would be the lowest pressure reading possible and bits representing the number 251 would be the highest pressure reading possible. Bits representing the numbers 252 to 255 that are transmitted from the A to D converter 12 are converted to the number 251 by the microprocessor 14. This leaves the bits representing numbers 252 to 255 free as designators for special functions. For example, when the start recording button 20*a* is depressed, the binary equivalent of the number 254 would be transferred to microprocessor 14 from control button 20*a* indicating that the data present at the A to D converter 12 should be stored. If the stop recording button 20*b* is depressed, the microprocessor 14 will stop storing data supplied by the A to D converter 12. It should be noted that the stop recording signal from button 20*b* is not represented by any of the numbers 0–255. The microprocessor 14 is instructed to stop recording data independently of the numbers 0 to 255. Similarly, the send data button 20*d*, instructs the microprocessor 14 to send the data to the microcomputer 26 independently of the numbers 0 to 255. Number 255 is used to record any patient observations. For instance, if there were a particular pressure increase as sensed by transducer 10, then the patient, if she also sensed this pressure increase, would press the patient mark button 20*c* which would in turn supply the microprocessor 14 with a binary equivalent to the number 255. Upon later analysis, this information would be analyzed to determine if an acutal pressure increase occurred at the point where the patient believed that it occurred. Bits equivalent to numbers 252 and 253 are reserved for future special functions.

When an event occurs, such as the depression of the start recording button 20*a*, the microprocessor 14 looks at the data supplied by the continuous time clock 16 and correlates the continuous time clock data with the event. During a data recording, the data supplied by the A to D converter 12 is correlated at periodic intervals in the microprocessor 14, to the time data supplied by the continuous time clock 16. Similarly, when the stop recording button is pushed, that event is correlated with the time supplied by the continuous time clock 16. The data gathered during the recording period is stored in the microprocessor 14. When the storage memory of the microprocessor 14 is full, no further recordings will be possible.

After the recording is complete, the data must be transmitted to the location where the microcomputer 26 is located. Typically, the A to D converter 12, the microprocessor 14, the continuous time clock 16, the modem 18 and the control buttons 20*a* to *d* are housed in a remote portable unit which is in turn connected by wires to the transducer 10.

In the system of the present invention, a phone call is made by the patient to the location of the microcomputer 26 typically a doctor's office, and voice communication is established. The patient's phone is then placed in the built-in modem 18 and the send data button 20*d* is depressed causing the data stored in the microprocessor 14 to be transmitted via the modem 18 over the phone lines 22 to a receiving modem 24 and then into the microcomputer 26. The modems 18 and 24 are typically 300 baud modems such a Bell 103 type including single chip equivalents such as Texas Instruments TMS99532 or Motorola MC14412. The information stored and transmitted by the microprocessor 14 is then received and processed by the microcomputer 26. To determine the relative time between various events that have occurred, the microcomputer 26 will subtract the various event times from the last event time recorded which is typically the time that the data is transmitted from the microprocessor 14 to the microcomputer 26. Thus, the microcomputer 26 will determine that the first event was the start of the data recording by the microprocessor 14. A printout from the microcomputer 26 will state something such as "start data recording 01 days 08 hours 22 minutes ago". The age of any particular datum recorded can also be determined from periodic time markers printed across the bottom of the strip.

If the real time clock 16 is reset in between the time the data is recorded and the time the data is transmitted, then subtracting the first event time from the last event time will result in a negative number. Anytime the microcomputer 26 detects that a negative number has been generated, it will automatically add to the last event time the maximum time cycle of the continuous time clock 16 before the first event time is subtracted. Thus, the relative time of any event can be determined even if the data is recorded in a first continuous time clock cycle and is transmitted in a second continuous time clock cycle.

If it is desired to know the wall clock time when an event occurred, then an operator of the microcomputer 26 can mark on a paper recording generated by the microcomputer 26 the wall clock time when the data is sent. The recorded wall clock time will correspond to the last event time recorded by the microprocessor 14. By comparing the relative time calculated by the microcomputer 26 with the wall clock time, it can be determined on what particular day and what particular hour and minute the event actually occurred. Similarly, if the microcomputer 26 has access to wall-clock time, it can automatically make the time calculations for the operator. However, as explained before, wall clock time is not a necessary piece of information in order to record the relative time between various events.

Figure 2:
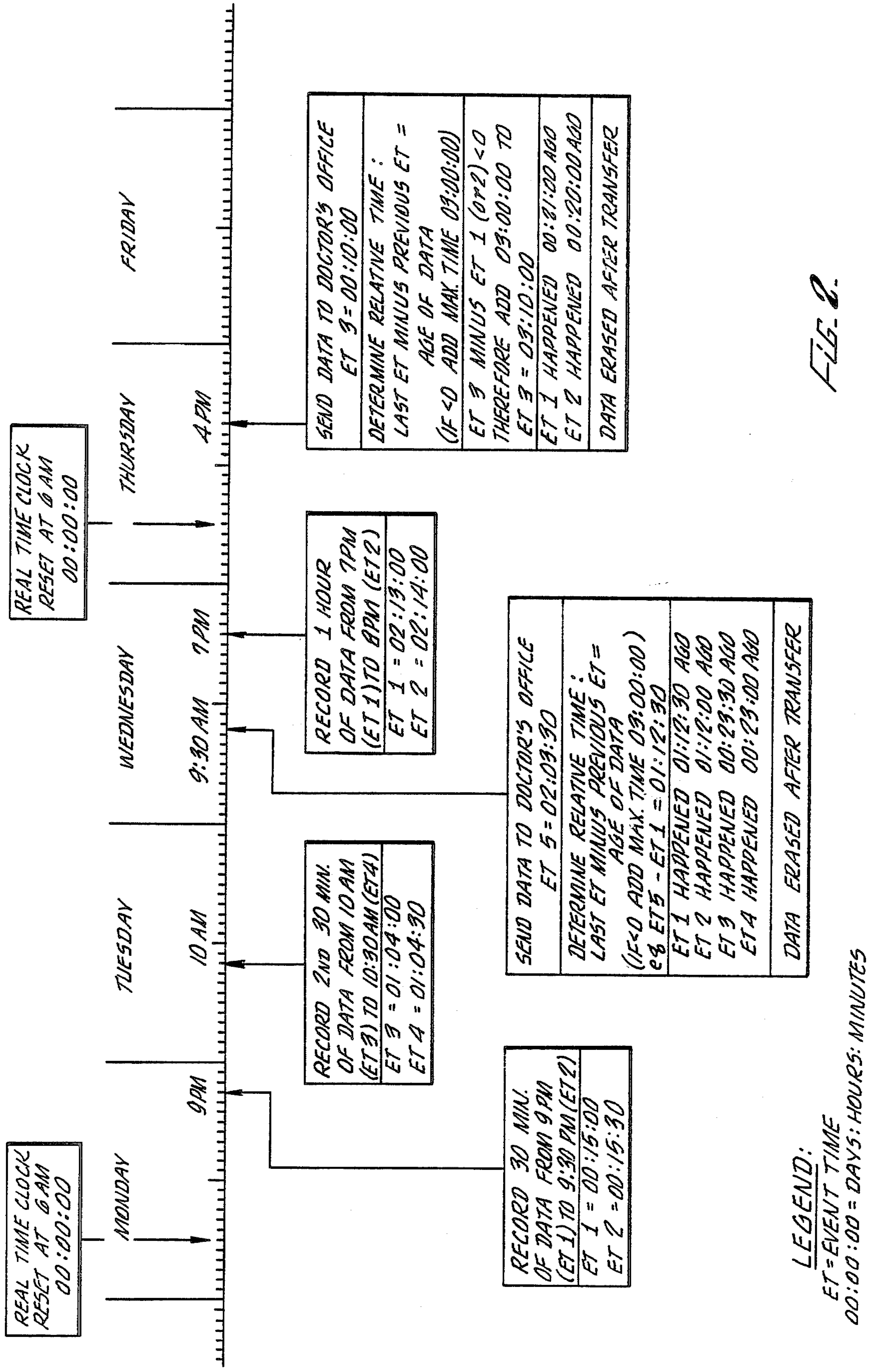
FIG. 2 is a time line diagram disclosing the function of the relative time clock under various conditions.

Turning now to FIG. 2, FIG. 2 is a time line drawing which, by way of example, diagrams the various events as they occur in relation to the time recorded by the continuous time clock 16 of FIG. 1. As can be seen from the diagram, by subtracting various event times from the last event time recorded, typically the sending of the data to the microcomputer 26, the relative time or age of any datum is determinable. Similarly, if data is recorded in one cycle of the continuous time clock and is transmitted in the next cycle of the continuous time clock, the maximum cycle time of the continuous time clock 16 is added to the last event time recorded. The previous event times are subtracted from that value which reveals how long ago an event occurred.

While a preferred embodiment of the present invention has been illustrated and described, modifications and variations thereof will be apparent to those skilled in the art given the techniques herein, and it is intended that all modifications and variations be encompassed within the scope of the appended claims.

What is claimed is:

1. A relative time clock device comprising continuous time clock means adapted to count in units of time for a fixed period and reset and repeat said count, event generator means adapted to supply event data corresponding to events, control means adapted to supply control signals, event correlator means connected to said continuous time clock means, to said event generator means and to said control means and adapted to correlate said event data and control signals with said units of time and then store the correlated event data and control signals as correlated signals, said correlated signals including a last correlated signal and at least one previous correlated signal, and event processor means adapted to be connected to said event correlator means for receiving said correlated signals and for determining the relative time between said correlated signals by subtracting from the time correlated to said last correlated signal the time correlated to a previous correlated signal.

2. A relative time clock as in claim 1 wherein said event processor means includes means to determine the relative time between said correlated signals when said last correlated signal occurs after said continuous time clock means is reset and said previous correlated signal occurs before said continuous time clock means is reset by adding said fixed period to said units of time correlated to said last correlated signal before the units of time correlated to said previous correlated signal are subtracted from the units of time correlated to said last correlated signal.

3. A relative time clock device for measuring and recording intrauterine pressure comprising continuous time clock means adapted to count in units of time for a fixed period of days and to reset and repeat said count, pressure transducer means adapted to supply an analog signal corresponding to intrauterine pressure, converter means connected to said pressure transducer means for receiving said analog signal and converting said analog signal to a digital signal, control means adapted to supply control signals comprising a start recording signal, a stop recording signal and a transmit data signal, event correlator means connected to said continuous time clock means, to said control means and to said converter means and adapted to correlate said digital signal and said control signals with said units of time and to record the correlated digital and control signals as correlated signals, said correlated signals including a last correlated signal and at least one previous correlated signal, said event correlator means being adapted to start recording correlated signals in response to said start recording signal and to stop recording correlated signals in response to said stop recording signal and to transmit said correlated signals in response to said transmit data signal, and event processor means adapted to be connected to said event correlator means for receiving said correlated signals and for determining the relative time between said correlated signals by subtracting from the time correlated to the last correlated signal the time correlated to any previous correlated signal, said event processor means includes means to determine the relative time between correlated signals when said last correlated signal occurs after said continuous time clock means is reset and said previous correlated signal occurs before said continuous time clock means is reset by adding said fixed period of days to said units of time correlated to said last correlated signal before the time correlated to said previous correlated signal is subtracted from the time correlated to said last correlated signal.

4. A relative time clock device comprising a continuous time clock adapted to count in units of time for a fixed period of days and reset and repeat said count a plurality of times, a pressure transducer adapted to supply an analog signal, analog to digital converter connected to said pressure transducer for receiving said analog signal and converting said analog signal to a digital signal, control means adapted to supply control signals comprising a start recording signal, a stop recording signal and a transmit data signal, said correlated signals including a last correlated signal and at least one previous correlated signal, an event correlator connected to said continuous time clock, to said control means and to said analog to digital converter and adapted to correlate said digital signal and said control signals with said units of time and to record the correlated digital and control signals as correlated signals, said event correlator being adapted to start recording correlated signals in response to said start recording signal and to stop recording correlated signals in response to said stop recording signal and to transmit said correlated signals in response to said transmit data signal, and an event processor adapted to be connected to said event correlator for receiving said correlated signals and for determining the relative time between said correlated signals by subtracting from the time correlated to the last correlated signal the time correlated to any previous correlated signal, said event processor including means to determine the relative time between the correlated signals when said last correlated signal occurs after said continuous time clock is reset and said previous correlated signal occurs before said continuous time clock is reset by adding said fixed period of days to said units of time correlated to said last correlated signal before the time correlated to said previous correlated signal is subtracted from the time correlated to said last correlated signal.

5. A method of measuring relative time including the steps of counting in units of time for a fixed period of days and resetting and repeating said count, generating an analog signal corresponding to pressure, receiving said analog signal and converting said analog signal to a digital signal, generating control signals comprising a start recording signal, a stop recording signal and a transmit data signal, correlating said digital signal and said control signals with said units of time, recording the correlated digital and control signals as correlated signals in response to said start recording signal and said stop recording signal, said correlated signals including a last correlated signal and at least one previous correlated signal, transmitting said correlated signals in response to said transmit data signal, and receiving said correlated signals and determining the relative time between said correlated signals by subtracting from the time correlated to the last correlated signal the time correlated to any previous correlated signal and determining the relative time between the correlated signals when said last correlated signal occurs after said continuous time clock is reset and said previous correlated signal occurs before said continuous time clock is reset by adding said fixed period of days to said units of time correlated to said last correlated signal before the time correlated to said previous correlated signal is subtracted from the time correlated to said last correlated signal.

* * * * *